United States Patent [19]

Gehrke et al.

[11] Patent Number: 4,948,731
[45] Date of Patent: Aug. 14, 1990

[54] MODIFIED TRANSCRIPTIONALLY ACTIVE SP6 PLASMID VECTOR

[75] Inventors: Lee Gehrke, Framingham, Mass.; Robert T. Fraley, St. Louis; Stephen G. Rogers, Chesterfield, both of Mo.

[73] Assignee: Massachusetts Institute of Technology, Cambridge, Mass.

[21] Appl. No.: 893,482

[22] Filed: Aug. 5, 1986

[51] Int. Cl.$^5$ .................. C12N 1/00; C12N 15/00; C12N 1/22; C12N 1/20; C12P 19/34; C12P 12/06; C07H 15/12

[52] U.S. Cl. ..................... 435/91; 435/320; 435/172.3; 435/69.1; 435/252.33; 435/253.6; 935/24; 935/41; 935/56; 935/73; 935/27; 536/27

[58] Field of Search .............. 435/91, 172.1, 172.3, 435/320, 253; 536/27; 935/3, 27, 38, 39, 41, 72

[56] References Cited

U.S. PATENT DOCUMENTS

4,766,072  8/1988  Jendrisak et al. ............. 435/91

OTHER PUBLICATIONS

Itakura et al, Science, vol. 209, pp. 1401–1405 (1980).
Jobling, S. A., Nucl. Acids Res., vol. 18, pp. 4483–4498 (1988).
Janda, M. et al, Virology, vol. 158, pp. 259–262 (1987).
Ahlquist, P. et al, Mol. Cell. Bio., vol. 4, pp. 2876–2882 (1984).
"Synthesis of Infectious Poliovirus RNA by Purified T7 RNA Polymerase", by S. Van Der Werf et al, Proc. Natl. Acad. Sci., U.S.A., 83, 2330–2334 (1986).
"Bacteriophage SP6–14 Specific RNA Polymerase", by E. T. Butler et al, J. Biol. Chem., 257, 5772–5778 and 5779–5788 (1982).
"Efficient in Vitro Synthesis of Biologically Active RNA and RNA Hybridization Probes from Plasmids Containing a Bacteriophage SP6 Promoter", by D. A. Melton et al, Nucl. Acids Res., 12, 7035–7056 and 7057–7070 (1984).

*Primary Examiner*—Robin L. Teskin
*Assistant Examiner*—Joan Ellis
*Attorney, Agent, or Firm*—Kilpatrick & Cody

[57] ABSTRACT

A recombinant plasmid which may be used for propagation of cloned cDNAs and also for the in vitro synthesis of RNA which is an exact copy of the natural sequence, wherein the transcript is devoid of vector-derived sequence. The novel vector was generated de novo by genetic engineering procedures using a synthetic double strand oligodeoxyribonucleotide fragment and a larger DNA fragment derived from plasmid pSP64. The vector, plasmid pHST-O, carried by *Escherichia coli* HB101, deposited with the ATCC on Dec. 30, 1985 and designated ATCC 53381, is distinguished from other vectors containing the SP6 promoter by the following characteristics: it contains a unique site for the restriction endonuclease BglII; the engineered GBlII site overlaps the downstream border of the SP6 promoter sequence; and the presence and positioning of the BglII restriction site permit insertion of cDNA molecules in such a way that transcription by the SP6 RNA polymerase begins exactly at the 5' terminus of the RNA, providing that the 5' terminal nucleotide of the mRNA transcript is a guanosine (G) residue, thus excluding the transcription of nucleotides derived from the vector. The novel vector permits synthesis of RNA molecules which have a defined 5' terminus and which are devoid of vector-derived sequence. The vector has potential use in research in molecular biology and in the in vitro production of RNA and proteins.

11 Claims, 3 Drawing Sheets

MODIFIED TRANSCRIPTIONALLY ACTIVE SP6 PLASMID VECTOR

BACKGROUND OF THE INVENTION

The Government has rights in this invention by virtue of the United States Department of Agriculture Grant No. 83-CRCR-1-1275 and National Institute of Health Grant No. NIH-1RO1-GM34370.

An RNA polymerase II enzyme, derived from a female-specific Salmonella bacteriophage, SP6 RNA polymerase, has been characterized by Butler and Chamberlin in *J. Biol. Chem.* 257, 5772-5778 (1982) and Kassavetis, et al, in *J. Biol. Chem.* 257, 5779-5788 (1982). This polymerase recognizes and binds to a DNA sequence called the SP6 promoter. The DNA-protein recognition process is remarkably stringent and is characterized by near absolute specificity. The SP6 RNA polymerase transcribes DNA into RNA. The SP6 promoter sequence, flanked by a polylinker region containing convenient restriction enzyme sites, has been introduced into a pBR322 plasmid derivative to form plasmid pSP64. Plasmid pSP64 is described by D. A. Melton, et al in *Nucl. Acids Res.* 12, 7035-7056 (1984) and P. A. Krieg et al in *Nucl. Acids Res.* 12, 7057-7070 (1984) and is commercially available in various forms from Promega Biotec, Madison, Wisc.; Bethesda Research Labs, Gaithersburg, Md.; Boehringer Mannheim, Indianapolis, Ind.; and International Biotechnologies, Inc., New Haven, Conn.

It is very difficult to isolate large quantities of pure RNA for research or applied use. This is particularly true with mRNA since mRNA comprises only a few percent of the total cellular RNA. Isolation is further impeded by the nearby ubiquitous presence of ribonucleases. It is much easier to clone a DNA fragment, subclone the DNA fragment into a vector containing a promotor sequence such as the SP6 promoter and then synthesize in vitro microgram quantities of pure RNA. This methodology has been widely used for research involving RNA processing, mRNA translation, and for production of single strand hybridization probes.

In plasmid pSP64, the transcriptional start site, a 5' guanosine, is separated from the first restriction cleavage site in the polylinker region by 5 base pairs. When the cDNA of interest is cloned into the first restriction site, the transcribed RNA contains at least five extraneous ribonucleotide which are derived from the vector. It is frequently desirable to generate transcription products which exactly reflect the cloned DNA of interest, without the effect of extraneous, vector-derived nucleotides.

Other groups, as reported by Melton et al in *Nucl. Acids Res.* 12, 7035-7056 (1984), have previously demonstrated that alterations of as few as two nucleotides within the SP6 promoter sequence inactivates the promoter and concluded that a transcriptionally-active promoter containing a restriction enzyme cleavage site right at the initiating G could not be made.

Recently, Van der Werf et al. reported in *Proc. Natl. Acad. Sci. U.S.A.* 83, 2330-2334 (1986) the construction of a vector containing the promoter for the related bacteriophage T7. This plasmid reportedly permits synthesis of mRNA containing as few as two extraneous nucleotides However, the authors note that the transcriptional start point has not been rigorously determined.

It is therefore an object of the present invention to provide a method for constructing a recombinant plasmid which ma be used for propagation of cloned cDNAs and for in vitro synthesis of RNA which is an exact copy of the natural sequence.

It is another object of the present invention to provide a recombinant plasmid which may be used for propagation of cloned cDNAs and for in vitro synthesis of RNA which is devoid of vector-derived sequence.

It is a further object of the invention to provide a novel vector which permits synthesis of RNA molecules which have a defined 5' terminus.

It is a still further object of the invention to provide a vector containing a unique site for a restriction endonuclease, such as BglII, adjacent a promoter sequence specifically recognized by an RNA polymerase.

SUMMARY OF THE INVENTION

A method for making a recombinant vector, and a recombinant plasmid, for the propagation of cloned cDNAs and for the in vitro synthesis of RNA which is an exact copy of the natural sequence, wherein the transcript is devoid of vector-derived sequence. The method for constructing a recombinant vector for making RNA transcripts devoid of vector sequence consists of: choosing a suitable vector containing an easily detectable marker, such as a DNA plasmid containing a selectable drug resistance marker; inserting a nucleotide sequence containing a promoter sequence specifically recognized by a RNA polymerase and a nucleotide sequence overlapping the promoter which is recognized by a restriction enzyme, such as a synthetic oligodeoxyribonucleotide containing a restriction site recognized by BglII, wherein the vector is devoid of other nucleotide sequence recognized by this restriction enzyme; and ligating the remaining sequence. Using this method, a unique restriction site is positioned immediately adjacent to the promoter sequence so that a nucleotide sequence of interest may be inserted into the construct in such a way that no vector nucleotides intervene between the transcriptional initiation site of the DNA polymerase and the true 5' terminus of the nucleotide insert, usually cDNA. The RNA polymerase will therefore copy the cDNA into an RNA which is devoid of vector sequence and an exact replica of the DNA of interest.

A novel plasmid was generated de novo by genetic engineering procedures using a synthetic double strand oligodeoxyribonucleotide fragment and a larger DNA fragment derived from plasmid pSP64. The plasmid, pHST-O, is distinguished from other vectors containing the SP6 promoter by the following characteristics: it contains a unique site for the restriction endonuclease BglII; the engineered BglII site overlaps the downstream border of the SP6 promoter sequence; and the presence and positioning of the BglII restriction site permit insertion of cDNA molecules in such a way that transcription by the SP6 RNA polymerase begins exactly at the 5' terminus of the RNA if the 5' mRNA terminus is a G, thereby excluding the transcription of nucleotides derived from the vector. Plasmid pHST-O in the host *E. coli* HB101 was deposited at the American Type Culture Collection, Rockville, Md. on Dec. 20, 1985 and designated ATCC 53381. The novel plasmid permits synthesis of RNA molecules which have a defined 5' terminus and which are devoid of vector-derived sequence. The vector has potential use in research in molecular biology and in the in vitro production of RNA and proteins.

DETAILED DESCRIPTION OF THE INVENTION

The present invention is a method for making a recombinant vector for use in the propagation of cloned cDNAs and for the in vitro synthesis of RNA devoid of vector-derived sequence. The essence of the method is to construct a vector having a promoter sequence and an unique restriction site overlapping the downstream border of the promoter; this design maintains the transcriptional activity of the promoter sequence and positions DNA inserts immediately adjacent to the promoter so that they are transcribed without extraneous vector nucleotides.

The method was used to make a recombinant plasmid, a small, autonomously-replicating circular molecule of double-strand DNA, for use in the propagation of cloned cDNAs and for the in vitro synthesis of RNA which is an exact copy of the natural sequence. The plasmid and its host *Escherichia coli* HB101 were deposited with the American Type Culture Collection, Rockville, Md. on Dec. 30, 1985 and assigned ATCC 53381.

Figure 1:
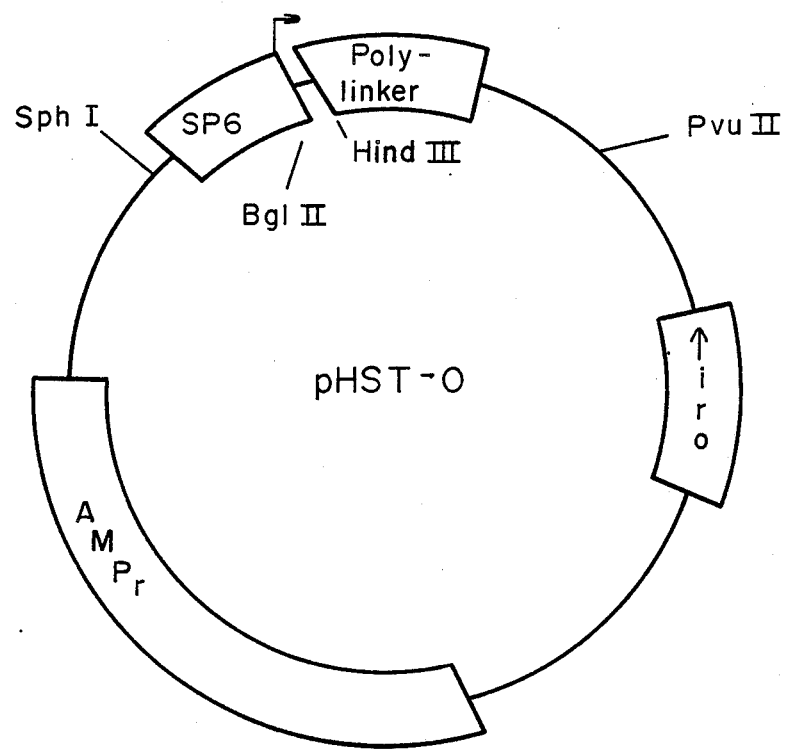
FIG. 1 is a schematic of plasmid pHST-O.

As shown in FIG. 1, plasmid pHST-O consists of a circular molecule of double-strand DNA containing a SphI restriction site, the SP6 promoter sequence with an overlapping BglII site, a polylinker region containing a HindIII restriction site separated from the transcriptional start site by five base pairs, a PvuII site, an origin of replication and an ampicillin resistance locus.

The plasmid, pHST-O, is a novel genetic molecule created by joining a 66 base pair synthetic oligodeoxyribonucleotide representing the SP6 promoter sequence with an overlapping BglII restriction endonuclease site to a pBR322 derivative plasmid DNA. The promoter is transcriptionally active. The new restriction site is positioned partially within the SP6 promoter, as demonstrated by inactivation of the promoter by cleavage of the vector with the restriction endonuclease BglII. It is possible to remove the BglII single-stranded cohesive termini with mung bean nuclease, followed by a blunt-end ligation of a fragment containing a 5' G to regenerate a transcriptionally active promoter. This manipulation changes all nucleotides separating the SP64 transcriptional initiation site in the polylinker region without inactivating the promoter.

Figure 2:
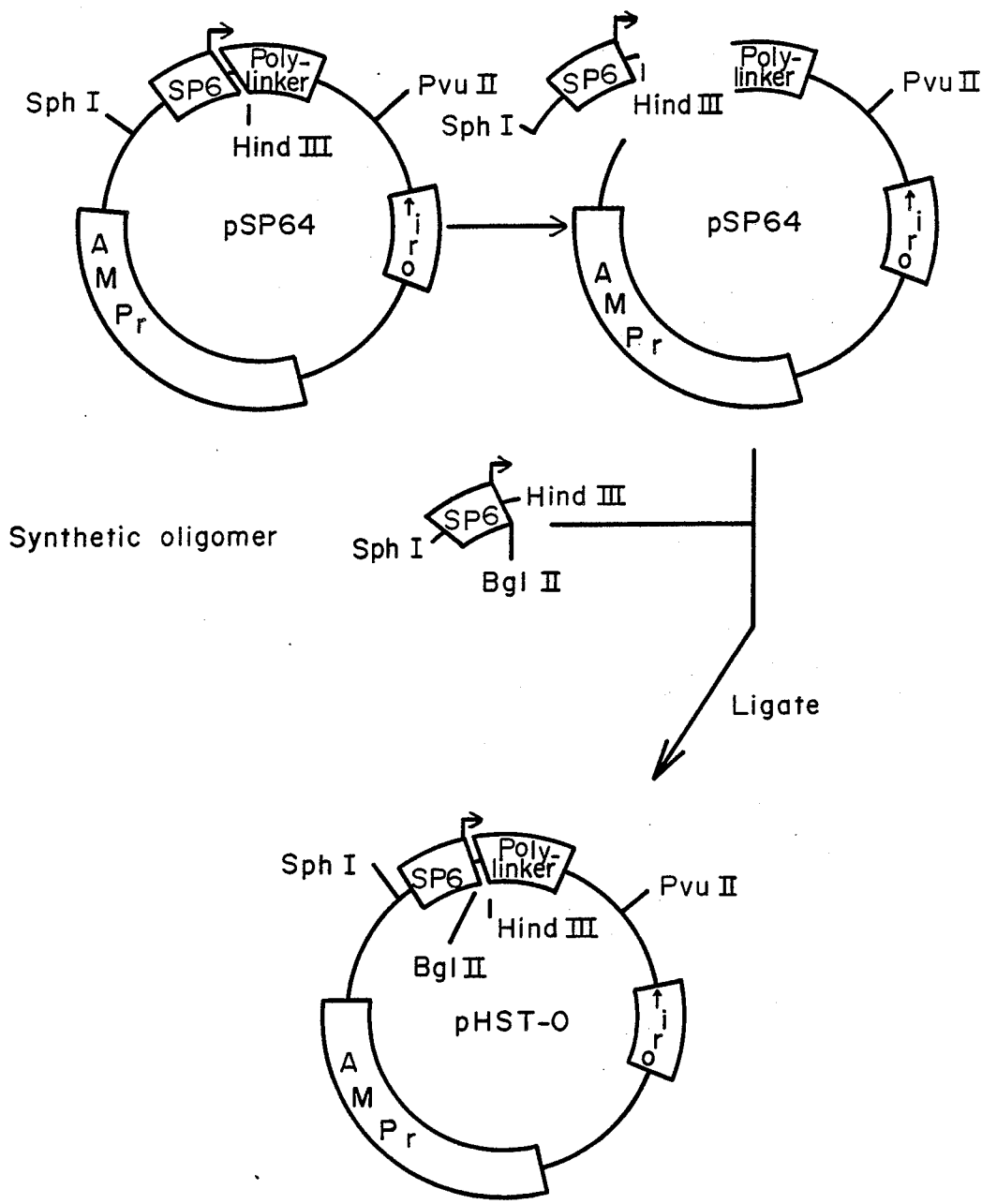
FIG. 2 is a schematic of the construction of plasmid pHST-O, shown in FIG. 1.

As shown in FIG. 2, the plasmid is constructed by first excising an SphI-HindIII fragment of approximately 450 base pairs containing the SP6 promoter sequence from plasmid pSP64 DNA, approximately 3,052 base pairs 5' phosphate groups were removed from the fragment and plasmid DNA by incubation of the DNA with calf intestinal alkaline phosphatase and the larger DNA fragment purified by electrophoresis into a 1% agarose gel. The region of the agarose gel containing the larger fragment is well separated from the promoter fragment. The region of the gel containing the larger fragment was excised and the DNA electroeluted into a dialysis bag using the method of T. Maniatis et al in *Molecular Cloning. A Laboratory Manual*, 64 (Cold Spring Harbor Laboratory, Cold Spring Harbor, N.Y. 1982). A synthetic oligomer containing sequences for the SP6 promoter and the overlapping BglII site was ligated into the cohesive SphI-HindIII termini and the ends covalently joined using T4 DNA ligase The circular DNA molecules were used for transformation of competent HB101 bacterial cells, described by D. Hanahan in *J. Mol. Biol.*, 166, 557 (1983).

The synthetic oligomer has the following sequence:

5' CCGGCTACAATTAATACATAACCTTATGTATCATACACATACG
3' GTACGGCCGATGTTAATTATGTATTGGAATACATAGTATGTGTATGC

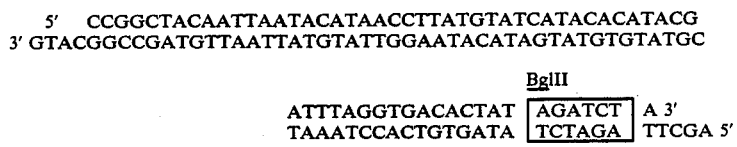

The two complementary strands were synthesized in an Applied Biosystems Model 380 " gene machine" and purified by high pressure liquid chromatography. The BglII site overlaps the right border of the SP6 promoter region. A 5' phosphate group was added to each oligomer by incubation with adenosine 5' triphosphate (ATP) and polynucleotide kinase, and the two strands annealed using the method of T. Maniatis in *Molecular Cloning. A Laboratory Manual*. Once annealed, the double-strand oligomer contained a SphI cohesive terminus and a HindIII terminus. Two hundred nanograms of the larger SP64-derived fragment and 10-fold molar excess of annealed oligomer were coprecipitated, solubilized, and ligated by incubation overnight at 15° C. in the presence of T4 DNA ligase. The ligated DNA was then used to transform competent HB101 bacterial cells. Transformants were screened by restriction mapping.

The presence of the BglII restriction site was demonstrated by cleavage with the enzyme BglII, followed by electrophoresis of the plasmid DNA into a 1% agarose gel. The electrophoretic patterns of the SP64 DNA, untreated or digested with HindIII or BglII, were compared. The comparison demonstrated the absence of a BglII site in pSP64 and the presence of the site in pHST-O.

The transcriptional activity of the SP6 promoter sequence in plasmid pHST-O was illustrated by analysis of transcription products on a 2% agarose gel as visualized by ethidium bromide staining pSP64 and pHST-O DNA were linearized with either BglI or PvuII. The RNAs transcribed from the pHST-O vector comigrate with the control RNAs transcribed from pSP64. Since there is no BglII site in pSP64 DNA, the SP6 polymerase transcribes a circular DNA. There are no transcription products when pHST-O DNA was cleaved with BglII, thereby verifying the proximity of the BglII site and the SP6 promoter.

Insertion of cDNAs to be transcribed from the exact 5' terminus requires removal of the BglII cohesive termini, followed by blunt end ligation of a DNA fragment with a 5' guanosine residue to restore the SP6 transcriptional start site.

Figure 3:
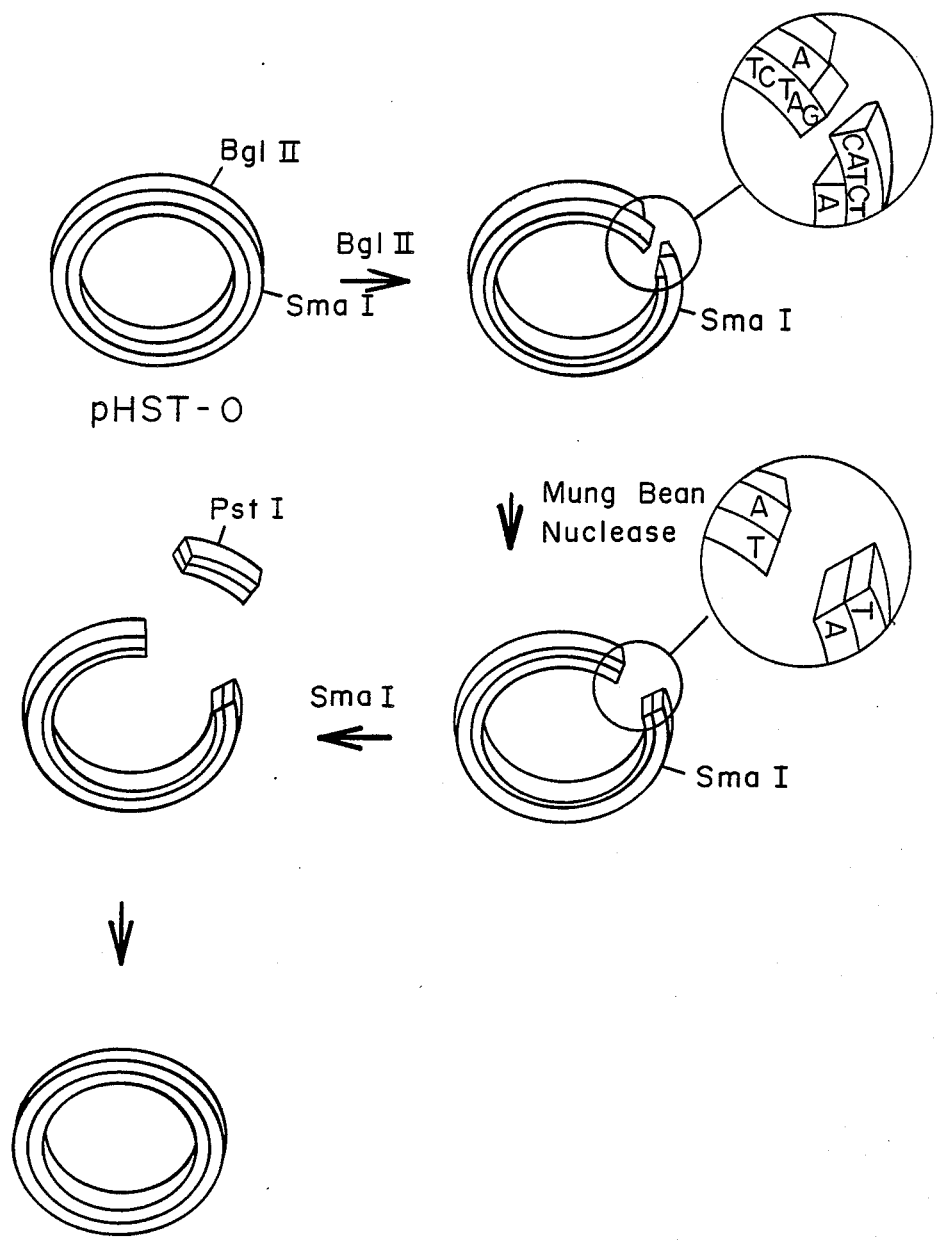
FIG. 3 is a schematic of the formation of blunt termini in plasmid pHST-O using mung bean nuclease.

FIG. 3 is a schematic representation of the formation of blunt termini using mung bean nuclease. pHST-O DNA is cleaved with BglII and the single-strand cohesive termini removed by digestion with mung bean nuclease. At this point, the vector is ready for ligation of the cDNA of interest. However, to test the transcriptional activity of the pHST-O DNA and to map the transcriptional start site, the DNA is cleaved with SmaI, a restriction enzyme which creates a blunt end with a 5' G(CCC/GGG) and, in this case, cleaves in a unique position about 45 base pairs downstream from the BglII site. The two blunt ends are ligated using T4 DNA ligase and circular plasmid DNA used to transform competent HB101 bacterial cells. Transformants are screened for the loss of the BglII site and for the loss of the PstI site, contained on the small BglII-SmaI fragment.

Plasmid DNA was then prepared and linearized with PvuII before transcribing the DNA with SP6 polymerase. The PvuII cut DNAs are transcribed with SP6 polymerase in the presence of alpha-32P-GTP and analyzed by electrophoresis into a 5% Nusieve agarose (FMC Corporation, Rockland, Me.) gel. The gel is dried and exposed to X-ray film. The PvuII transcription product using pSP64 template DNA is about 245 nucleotides. However, digestion of the mung-bean nuclease treated DNA with SmaI removes a 45 base pair DNA fragment. It was expected that the RNA transcriptional product would have therefore been slightly smaller. The presence of a transcriptional product from the pHST-O vector demonstrates that the promoter is active after removal of the BglII cohesive termini and replacement with a different nucleotide sequence derived from the SmaI site. The fact that the RNA is slightly smaller than the control further indicates that the G serving as the transcriptional start site is derived from the nucleotides comprising the SmaI site, and that the BglII-SmaI fragment containing the original initiation site has been removed. Sequencing was used to confirm the location of the transcriptional start site near the former BglII site. This also demonstrated that a restriction site other than for BglII could be uitilized.

The same method may be used to construct other plasmids by insertion of a restriction enzyme site overlapping the SP6 promoter without altering the internal region of the promoter itself to generate a transcriptionally active promoter with a flanking restriction site. For example, a vector based upon generation of a site for the restriction enzyme StuI (AGG/CCT) may be constructed. The oligodeoxyribonucleotide sequence representing the SP6 promoter with an overlapping StuI site has the following structure:

Unfortunately, transcription of this sequence does not always proceed uniformly. This "stuttering" can produce a heterogeneous group of transcribed sequences.

A related bacteriophage, T7, has a promoter sequence which is similar to that of SP6. There is almost complete phylogenetic conservation of sequences upstream of the transcriptional start site. There is almost total divergence downstream of the transcriptional start site. The same method used to construct the pHST-O vector may be used to insert an overlapping restriction site in vectors containing the T7 promoter. The advantage to using vectors containing the T7 promoter is that the T7 polymerase is much less expensive than the SP6 polymerase.

Although this invention has been described with reference to specific embodiments, it is understood that modifications and variations of the disclosed methods and products may occur to those skilled in the art. It is intended that all such modifications and variations be included within the scope of the appended claims.

I claim:

1. A transcriptionally active vector comprising a SP6 bacteriophage promoter sequence, and a unique site for a restriction endonuclease, said restriction site overlapping the downstream border of the promoter sequence 3', to and including the transcription initiation site G, wherein cleavage of said restriction site and insertion and transcription of a DNA sequence containing a 5', G downstream of the promoter sequence restores the transcriptional start site and results in a transcribed sequence not including nucleotite sequences derived from the vector.

2. The vector of claim 1 wherein said restriction site is a BglII site.

3. The vector of claim 2 comprising the following structure:

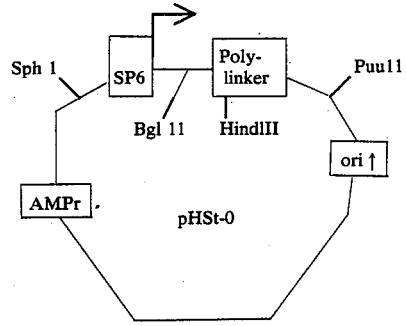

4. The plasmid of claim 3 as deposited with the American Type Culture Collection on Dec. 20, 1985 and designated as ATCC 53381.

5. The vector of claim 1 wherein said plasmid comprised the following sequence:

```
5'  CCGGCTACAATTAATACATAACCTTATGTATCATACACATACG
3'  GTACGGCCGATGTTAATTATGTATTGGAATACATAGTATGTGTATGC
```

```
                        STuI
    ATTTAGGTGACACTAT   AGGCCT    A 3'
    TAAATCCACTGTGATA   TCCGGA    TTCGA 5'
```

```
5'  CCGGCTACAATTAATACATAACCTTATGTATCATACACATACG
3'  GTACGGCCGATGTTAATTATGTATTGGAATACATAGTATGTGTATGC
```

```
                              BglII
        ATTTAGGTGACACTAT  AGATCT   A 3'
        TAAATCCACTGTGATA  TCTAGA   TTCGA 5'
```

6. The vector of claim 1 wherein said vector is a transcriptionally active plasmid containing a unique StuI site, said plasmid comprising the following sequence:

```
5' CCGGCTACAATTAATACATAACCTTATGTATCATACACATACG
3' GTACGGCCGATGTTAATTATGTATTGGAATACATAGTATGTGTATGC
```

```
                              STuI
        ATTTAGGTGACACTAT  AGGCCT   A 3'
        TAAATCCACTGTGATA  TCCGGA   TTCGA 5'
```

7. A method for constructing a recombinant vector for making RNA transcripts devoid of vector sequence comprising:
   (a) selecting a nucleotide sequence comprising a SP6 promotor sequence specifically recognized by the SP6 RNA polyerase, said promoter sequence including a transcription initiation site G, and a nucleotide sequence recognized by a restriction enzyme in the downstream portion overlapping the transcriptional initiation site;
   (b) inserting said SP6 promoter-restriction site sequence into a vector devoid of nucleotide sequence recognized by the restriction enzyme of step a; and
   (c) ligating the remaining sequences, wherein the presence and positioning of the restriction site permit insertion into the vector at the restriction site, and transcription, of a second nucleotide sequence including a 5' G, the transcribed second sequence being devoid of vector-derived nucleotide sequence.

8. The method of claim 7 further comprising inserting the second nucleotide sequence, wherein the resulting construct is devoid of vector nucleotides between the transcriptional initiation site of the RNA polymerase and the true 5' terminus of said second nucleotide sequence.

9. The method of claim 7 wherein the restriction enzyme is BglII.

10. The method of claim 7 wherein the vector of step (b) has a selectable drug resistance marker.

11. The method of claim 7 wherein said inserted second nucleotide sequence is a cDNA.

* * * * *